United States Patent [19]

Hübl et al.

[11] Patent Number: 4,897,415
[45] Date of Patent: Jan. 30, 1990

[54] 2-IMINO-1,3-DITHIETANES, THEIR USE AS PESTICIDES

[75] Inventors: Dieter Hübl; Ernst-Albrecht Pieroh; Eberhard Richter; Reinhold Puttner, all of Berlin, Fed. Rep. of Germany

[73] Assignee: Schering Aktiengesellschaft, Fed. Rep. of Germany

[21] Appl. No.: 149,414

[22] Filed: Jan. 29, 1988

[30] Foreign Application Priority Data

Jan. 30, 1987 [DE] Fed. Rep. of Germany ........ 3703213
Sep. 4, 1987 [DE] Fed. Rep. of Germany ........ 3730136

[51] Int. Cl.⁴ .................. C07D 331/04; A61K 31/385
[52] U.S. Cl. ...................... 514/430; 514/337; 514/452; 514/464; 514/465; 514/440; 549/89; 549/366; 549/440; 549/32; 546/268
[58] Field of Search .......................... 549/89; 514/430

[56] References Cited

U.S. PATENT DOCUMENTS

| | | | |
|---|---|---|---|
| 3,842,096 | 10/1974 | Brand et al. ........................ | 549/89 |
| 3,914,428 | 10/1975 | Wilbur et al. ...................... | 549/89 |
| 3,915,962 | 10/1975 | Brand et al. ........................ | 549/89 |
| 3,928,382 | 12/1975 | Addor et al. ....................... | 549/89 |
| 3,954,801 | 5/1976 | Addor et al. ....................... | 549/89 |

*Primary Examiner*—Jane T. Fan
*Attorney, Agent, or Firm*—Ostrolenk, Faber, Gerb & Soffen

[57] ABSTRACT

There are described new 2-imino-1,3-dithietanes of general formula I

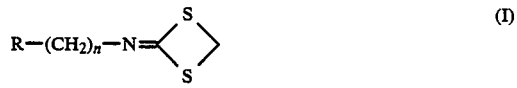

in which
R is the group

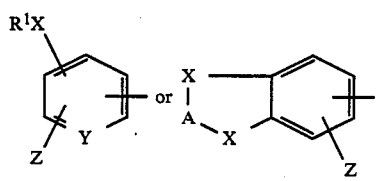

in which
A is CFHal, C(CH$_3$)C$_{1-4}$-alkyl, C(CH$_3$)CHal$_3$, C(CH$_3$)CF$_2$Cl, C(CH$_3$)CFCl$_2$, C$_2$H$_4$, C$_2$H$_3$Hal, C$_2$H$_2$Hal$_2$, C$_2$HHal$_3$, C$_2$F$_2$Cl$_2$, C$_2$F$_4$ or C$_2$F$_3$Cl, in which Hal is F or Cl, Y is nitrogen or CH, R$^1$ is fluoro-C$_{1-12}$-alkyl, fluoro-C$_{2-12}$-alkenyl, fluoro-C$_{2-12}$-alkynyl, fluorocyclopropyl or fluorocyclopropylmethyl;

X is oxygen or sulphur, 2 is defined in the specification and n is 0, 1 or 2, as well as their acid addition salts, a process for their preparation and their use as pesticides. The new compounds are especially useful as nematicides.

18 Claims, No Drawings

2-IMINO-1,3-DITHIETANES, THEIR USE AS PESTICIDES

The invention relates to new 2-imino-1,3-dithietanes, their preparation according to known methods and their use as pesticides, especially against nematodes.

Compounds of similar structure with nematicidal activity are known, as for example in U.S. Pat. No. 3,484,455.

However the known compounds have the disadvantage that either they are not sufficiently compatible to plants or they are not sufficiently active.

The object of the present invention is the preparation of new compounds that have good activity, especially against nematodes, without at the same time being incompatible with plants.

It has now been found that 2-imino-1,3-dithietanes of general formula I

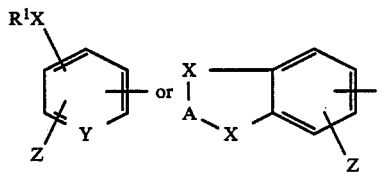

(I)

in which
R is the group

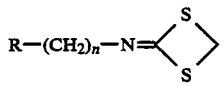

in which
A is CFHal, C(CH$_3$)C$_{1-4}$-alkyl, C(CH$_3$)CHal$_3$, C(CH$_3$)CF$_2$Cl, C(CH$_3$)CFCl$_2$, C$_2$H$_4$, C$_2$H$_3$Hal, C$_2$H$_2$Hal$_2$, C$_2$HHal$_3$, C$_2$F$_2$Cl$_2$, C$_2$F$_4$ or C$_2$F$_3$Cl, in which Hal is F or Cl, Y is nitrogen or CH, R$^1$ is fluoro-C$_{1-12}$-alkyl, fluoro-C$_{2-12}$-alkenyl, fluoro-C$_{2-12}$-alkynyl, fluorocyclopropyl or fluorocyclopropylmethyl;

X is oxygen or sulphur,

Z is hydrogen, halogen, C$_{1-6}$-alkyl, C$_{1-6}$-alkoxy, C$_{1-6}$-alkylthio, di-C$_{1-6}$-alkylamino, halo-C$_{1-6}$-alkyl, halo-C$_{1-6}$-alkoxy, halo-C$_{1-6}$-alkylthio, C$_{1-6}$-alkoxycarbonyl, halo-C$_{1-6}$-alkoxycarbonyl, nitro, cyano, amino, phenoxy, halophenoxy, phenylthio or halophenylthio, and n is 0, 1 or 2, as well as their acid addition alts, show a surprisingly good nematicidal activity whilst at the same time having good plant compatibility.

The compounds of the invention further show good activity against biting and sucking insects as well as against insect eggs and mites.

The acid addition salts of the compounds of the invention of formula I can be derived from inorganic and organic acids. Examples are hydrochloric acid, hydrobromic acid, hydroiodic cid, sulphuric acid, mono and difunctional carboxylic acids and hydroxycarboxylic acids, such as for example acetic acid, trifluoroacetic acid, maleic acid, fumaric acid and citric acid, as well as sulphonic acids, such as for example p-toluenesulphonic acid, 1,5-naphthalendisulphonic acid and trifluoromethanesulphonic acid.

By the terms halogen is to be understood fluorine, chlorine, bromine and iodine.

The designation fluoralkyl, fluoralkenyl, fluoralkynyl, fluorocyclopropyl and fluorocycloproplymethyl means that one or more hydrogen atoms of the alkyl, alkenyl, alkynyl or cyclopropyl group is replaced by fluorine.

The compounds of the invention of formula 1 can be prepared by known methods in which an amine of formula II.

(II)

in which R and n have the same meaning as in formula I, is reacted with carbon disulphide, in the presence of a base, to give a dithiocarbamate of formula III

(III)

in which M$^\oplus$ is an alkali metal ion or a protonated tertiary amine, and then the dithiocarbamate, so obtained, is reacted with dibromo- or diiodomethane in the presence of a base and optionally with an organic or inorganic acid to give the corresponding acid addition salt.

The reaction of the amine to the dithiocarbamate can be carried out either in the absence of a solvent or in the presence of an inert solvent, such as tetrahydrofuran or diethyl ether, in the temperature range 0° to 70° C.

The reaction of the dithiocarbamate with dibromomethane or diiodomethane is generally carried out by reacting the dithiocarbamate of formula III in an organic solvent, such as dimethylformamide or tetrahydrofuran, with the addition of a base, at a temperature in the range −10° C. to 70° C., in which the ratio of dihalomethane to the compound of formula III is from 1:1 to 1:7.

The reaction time is about 0.5 to 20 hours. The reaction mixture is then poured into ice/water and extracted several times with diethyl ether or ethyl acetate. The combined organic phases are then dried over magnesium sulphate and concentrated. The resulting crude product can be purified in conventional manner by recrystallisation, vacuum distillation or column chromotography.

The amines of formula II, used as starting materials, are either known or can be prepared by known processes, e.g. DE-OS 32 23 505 amd 33 15 147.

The compounds of the invention are, as a rule, slightly yellow crystals or viscous oils that are almost insoluble in water but are generally soluble in organic solvents.

The acid addition salts can be obtained in conventional manner, for example by dissolving the 2-imino-1,3-dithietane in a suitable solvent and adding the corresponding acid.

Because of the nematicidal activity coupled with good plant compatibility, the compound according to the invention can be successfully applied in plant protection as pesticides in agriculture, in vine and fruit growing, in horticulture and in forestry.

Plant parasitic nematodes which can be controlled according to the invention include for example root-knot nematodes, such as *Meloidogyne incognita, Meloidogyne hapla* and *Meloidogyne javanica*, cyst forming nematodes, such as *Globodera rostochiensis, Heterodera schacktii, Heterodera avanae, Heterodera glycines* and *Heterodera trifolii*, and stem and leaf eelworms, such as *Ditylenchus dipsaci, Ditylenchus destructor, Aphelenchoides ritzemabosi, Pratylenchus neglectus, Pratylenchus penetrans, Pratylenchus curvitatus*, as well as *Tylenchorhynchus dudius, Tylenchlorhynchus claytoni, Rotylenchus robustus, Heliocotylenchus multicinctus, Radopholus similis, Belonolaimus longcaudatus, Longidorus elongatus* and *Trichodorus primitivus*.

Because of their insecticidal and acaricidal properties, the compounds of the invention offer the possibility of uses in the treatment against pests of various stages of growth of crop plants, as well as also pests of humans and animals.

The active ingredients of the invention can be used in the form of their commercial formulations and/or in the form of preparations obtained from these formulations.

The content of active ingredient used in the preparations prepared from the commercial formulations can vary over wide ranges. The rate of use of combating per hectare lies between about 0.03 kg to about 10 kg preferably about 0.3 kg to about 6 kg.

The active ingredient can be applied in the usual formulations such as solutions, emulsions, wettable powders, suspensions, powders, dusts, foams, pastes, soluble powders, granules, aerosols, suspension concentrates, seed dressings, natural and synthetic substances impregnated with the active ingredients, microcapsules in polymers and in seed coatings for seeds, as well as formulations with burning substances such as smoke cartridges, smoke capsules and smoke spirals amongst others as well as ULV-cold and hot fogging formulations.

These formulations can be prepared in known manner for example by mixing the active ingredient with diluents such as liquid solvents, and liquified gases and/or solid carriers, optionally using surface active agents such as emulsifiers and/or dispersing agents and/or foaming agents.

When using water as the diluent, organic solvents can also be used for example as auxiliary solvents.

Examples of liquid solvents include aromatic hydrocarbons, such as xylene, toluene or alkynaphthalene, chlorinated aromatic or chlorinated aliphatic hydrocarbons, such as chlorobenzene, chloroethylene or methylene dichloride, aliphatic hydrocarbons, such as cychlohexane or paraffins, for example mineral oil fractions, alcohols, such as butanol and glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water.

By the term liquefied gaseous diluents or carriers are meant those substances which are gaseous at normal temperature and pressure, for example aerosol blowing agents, such as halohydrocarbons, as well as butane, propane, nitrogen and carbon dioxide.

Examples of solid carriers are natural earth powders, such as kaolin, alumina, talc, chalk, quartz, attapulgite, montmorillonite or diatomaceous earths and synthetic powders, such as finely divided silica, aluminium oxide and silicates as well as solid carriers for granules, crushed and fractionated natural rocks, such as calcite, marble, pumice, sepiolith and dolomite, as well as synthetic granules from inorganic and organic powders as well as granules from organic materials such as sawdust, coconut shells, maize cobs and tobacco stalks.

Examples of emulsifying and/or foaming agents include non-ionic and anionic emulsifiers, such as polyoxyethylene-fatty acid esters, polyoxyethylene-fatty alcohol ethers, for example alkylaryl-polyglycol-ethers, alkylsulphonates and arylsulphonates as well as protein hydrolysates.

Dispersing agents include for example lignin, sulphite waste liquors and methylcellulose.

There can also be used in the formulations sticking agents such as carboxymethylcellulose, natural and synthetic powdery, granulated or latex-forming polymers, as well as gum arabic, polyvinyl alcohol and polyvinyl acetate.

There can also be used dyestuffs, such as inorganic pigments, for example iron oxide, titanium oxide, ferrocyan blue and organic dyestuffs such as alizarin- and azo-metal phthalocyanine dyestuffs and trace elements such as salts of iron, manganese, boron, copper, cobalt, molybdenum and zinc.

The formulations contain in general between 0.1 and 95 weight percent of the active ingredient, preferably between 0.5 and 90 percent.

Examples of formulations are:

I. Wettable powder 10 parts by weight of the compound of Exaple 1 are intimately mixed with 12 parts by weight of calcium lignosulphonate, 76 parts by weight of finely divided kaolin and 2 parts by weight of dialkylnaphthalene sulphonate and then milled.

II. Dusting powder 2.5 parts by weight of the compound of Example 2 were dissolved in 10 methylene chloride and added to a mixture of 20 parts by weight of finely divided silicic acid and 71.5 parts by weight talc and 1 part by weight Sudan red. The solvent was removed in vacuo and the residue finely milled.

III. Granulate 5 parts by weight of the compound of Example 1 were dissolved in 10 parts by weight of methylene chloride and sprayed onto 95 parts by weight granulated attapulgite of particle size 0.3 mm–0.8 mm and dried.

IV. Emulsifiable concentrate 20 parts by weight of the compound of Example 4 were dissolved in a mixture of 75 parts by weight of isophorone and 5 parts by weight of a mixture of 30 parts by weight of calcium benzene sulphonate and 30 parts by weight of castor oil polyglycolate with 40 mole % ethylene oxide and 40 parts by weight of a copolymer of propylene- and ethylene oxide.

The following examples illustrate the preparation of compounds according to the invention.

EXAMPLE I 4-(4-Trifluoromethylthiophenyl)-1,3-dithietan-2-imine 11.0 g (0.057 mol) 4-Trifluormethylthioaniline and 4.60 g (0.060 mol) carbon disulphide were mixed together and, at room temperature over a period of 5 minutes, 6.07 g (0.060 mol) triethylamine was added dropwise. The resulting yellow crystal slurry was then stirred at 70° C. for 1 hour. After cooling it was treated with 50 ml diethyl ether, stirred vigorously and the crystals separated.

13.76 g (70.5% of theory) triethylammonium 4-trifluoromethylthiophenyldithiocarbamate were obtained.

13.76 g (0.40 mol) Triethylammonium 4-trifluoromethylthiophenyldithiocarbamate was dissolved in 50 ml dimethylformamide. With vigorous stirring, a mixture of 34.77 g (0.20 mol) dibromomethane and 4.0 g (0.040 mol) triethylamine in 20 ml dimethylformamide was added, dropwise. It was stirred at room temperature for 2 hours. The reaction mixture was then poured into 300 ml ice/water and extracted 3 times with a 100 ml diethyl ether. The combined ether phases were dried over magnesium sulphate and concentrated. The residue was purified using column chromatography (eluent: hexane/ethyl acetate 4:1).

Yield: 5.21 g=38.0% of theory
m.p.: 26°–28° C.

Preparation of the starting material 8.00 g (0.06 mol) 4-Aminothiophenol was introduced into an irradiation apparatus, manufactured by Hans Mangels-Destillationstechnik, D 5303-Bornheim-Roisdorf (apparatus 13/1, 100 ml with a Philips UV-lamp H PK 125 with a quartz glass filter) and at $-60°$ C. to $-70°$ C., about 40 ml ammonia and about 16 g (0.08 mol) trifluoromethyl iodide was condensed in. The reaction mixture was irradiated at $-60°$ C. for 1 hour, whilst stirring vigorously.

As the temperature rose, the ammonia evaporated off and the reaction solution was treated at room temperature with 25 ml 25% caustic soda and extracted 3 times with 50 ml diethyl ether. The organic phase was washed twice with 5% sodium thiosulphate solution, dried over magnesium sulphate and concentrated in vacuo.

11 g (94.9% of theory) 4-trifluoromethylthioaniline was obtained.

EXAMPLE 2

N-(4-Difluoromethoxyphenyl)-1,3-dithietan-2-imine 7.6 g (0.048 mol) 4-Difluoromethoxyaniline and 2.86 ml (0.048 mol) carbon disulphide were combined. Starting at 20° C., 7.16 ml (0.0525 mol) triethylamine was added dropwise, over 5 minutes, whereby the temperature rose to 35° C. The resulting yellow crystal slurry was stirred at 70° C. for 1 hour. After cooling 50 ml diethyl ether was added and the crystals separated off.

11 g (68.5% of theory) triethylammonium 2-(4-difluoromethoxyphenyl)dithiocarbamate was obtained.

11 g (0.033 mol) Triethylammonium 2-(4-difluoromethoxyphenyl)dithiocarbamate was dissolved in 40 ml dimethylformamide. Over 20 minutes, a mixture comprising 12.44 ml (0.178 mol) dibromoethane and 4.77 ml (0.034 mol) triethylamine in 20 ml dimethylformamide was added dropwise. It was stirred at room temperature for 2 hours. The reaction mixture was then poured into 500 ml ice/water and extracted 3 times with 100 ml diethyl ether. The combined ether phases were dried over magnesium sulphate, concentrated and purified by column chromatography (eluent: hexane/ethyl acetate 4:1).

Yield: 3.94 g=48.7% of theory
$n_{20}^D$: 1.6100.

Preparation of the starting material 26.1 g (0.19 mol) 4-Nitrophenol was dissolved in 120 ml 1,4-dioxane. At 20° C., 37.5 g (0.94 mol) sodium hydroxide, dissolved in 100 ml water, was added dropwise, whereby the temperature rose to about 60° C. At a bath temperature of 85° C., monochloridifluoromethane was introduced over 2 to 3 hours, with vigorous stirring. The reaction mixture, at the end of the treatment, was poured into 500 ml ice/water and extracted 3 times with 100 ml ethyl acetate. The combined organic phases were dried over magnesium sulphate.

30 g (84.6% of theory) 4-difluoromethoxynitrobenzene was obtained.

14.7 g (0.077 mol) 4-Difluoromethoxynitrobenzene was dissolved in a mixture of 180 ml ethanol and 110 ml water. It was added to 7.34 g (0.137 mol) ammonium chloride. At a temperature of 30° C. 36.98 g (0.566 mol) zinc powder was added portionwise. It was then stirred for another 1.5 hours. It was then separated from the undissolved material and the aqueous phase concentrated to half, extracted 3 times with 50 ml diethyl ether, dried over magnesium sulphate and concentrated.

8.72 g (70.5% of theory) 4-Difluoromethoxyaniline was obtained.

EXAMPLE 3

N-[2-(2,2,2-Trifluoroethoxy)-5-pyridyl]-1,3-dithietan-2-imine 8.8 g (0.048 mol) 2-(2,2,2-Trifluoroethoxy)-5-aminopyridine and 3.50 g (0.046 mol) carbon disulphide were combined. Over 5 minutes, 4.65 g (0.046 mol) triethylamine was added, dropwise. The reaction mixture was then stirred at 70° C. for 1 hour. After this 50 ml diethyl ether was added at room temperature. The resulting crystals were separated and dried.

12.0 g (70.6% of theory) triethylammonium N-[2-(2,2,2-trifluoroethoxy)-5-pyridyl]dithiocarbamate was obtained.

8.13 g (0.022 mol) triethylammonium N-[2-(2,2,2-trifluoroethoxy)-5-pyridyl]dithiocarbamate was dissolved in 50 ml dimethylformamide. With vigorous stirring, a mixture of 19.12 g (0.11 mol) dibromomethane and 2.23 g (0.022 mol) triethylamine in 20 ml dimethylformamide was added dropwise at 20° C. It was then stirred for a further hour and filtered from the undissolved material. The reaction mixture was poured into 300 ml ice/water and extracted 3 times with each of 50 ml diethyl ether. The ether extracts were dried over magnesium sulphate, concentrated in vacuo and the residue purified by column chromatography (eluent: hexane/ethyl acetate 4:1).

Yield: 3.45 g=64.0% of theory
m.p.: 52°–54° C.

Preparation of the starting material 15.85 g (0.10 mol) 2-Chloro-5-nitropyridine and 10.04 g (0.10 mol) 2,2,2-trifluoroethanol were dissolved in 100 ml of dimethylformamide. At 20° C., 12.34 g (0.11 mol) potassium tert-butylate was added portionwise. It was then stirred for 2 hours. The mixture was then poured into 500 ml ice/water and extracted 3 times with 50 ml ethyl acetate. The organic solvent extracts were dried over magnesium sulphate and concentrated.

20.5 g (92.3% of theory) 2-(2,2,2-trifluoroethoxy)-5-nitropyridine was obtained.

11.1 g (0.05 mol) 2-(2,2,2-trifluoroethoxy)-5-nitropyridine was dissolved in 70 ml ethanol and treated with 5.36 g (0.10 mol) ammonium chloride and 40 ml water added. At a temperature of 30°–40° C., 26.15 g (0.40 mol) zinc powder was added portionwise. It was then stirred at room temperature for 3 hours. The reaction mixture was filtered, the filtrate concentrated and taken up in 400 ml diethyl ether. The ether phase was washed 3 times with each of the 100 ml of water and then dried over magnesium sulphate and concentrated.

8.8 g (91.4% of theory) 2-(2,2,2-trifluoroethoxy)-5-aminopyridine was obtained.

In a similar manner the following compounds were prepared:

$$R-(CH_2)_n-N=\underset{S}{\overset{S}{\diagup}}, n = 0$$

| Example No | R | m.p. (C.) or $n_{20}^D$ |
|---|---|---|
| 4 | 2,2-difluorocyclopropyl-O-(4-phenyl)- | 39–40 |
| 5 | 2,2-difluorocyclopropyl-O-(phenyl)- | 45–47 |
| 6 | 2,2-difluorocyclopropyl-CH$_2$-O-(pyridyl)- | 1,6168 |
| 7 | CF$_3$—CH$_2$—O—(4-phenyl)- | 71–73 |
| 8 | CHF$_2$—CF$_2$—CH$_2$—O—(4-phenyl)- | 41–43 |
| 9 | CHF$_2$—CF$_2$—CH$_2$—O—(pyridyl)- | 42–43 |
| 10 | CHF$_2$O—(2,6-dichloro-4-phenyl)- | 48–49 |
| 11 | CCl$_3$—CF$_2$—O—(4-phenyl)- | 49 |
| 12 | (pyridyl)-OCH$_2$—CF$_3$ | 41–43 |
| 13 | CF$_3$—CH$_2$O—(3-methyl-4-phenyl)- | 33–35 |
| 14 | CHF$_2$S—(4-phenyl)- | 1,6643 |
| 15 | OCHF$_2$—(2-phenyl)- | 1,6062 |
| 16 | CF$_3$—CH$_2$O—(3-fluoro-4-phenyl)- | 62–65 |
| 17 | 4-Cl, 2-OCHF$_2$-phenyl | 61–64 |
| 18 | CHF$_2$O—(2-chloro-4-phenyl)- | 84 |
| 19 | CHF$_2$O—(3-phenyl)- | 1,6065 |
| 20 | OCHF$_2$, H$_3$C—(phenyl)- | 1,5800 |
| 21 | CHF$_2$—CF$_2$O—(4-phenyl)- | 34–36 |
| 22 | CF$_3$—CH$_2$—S—(4-phenyl)- | 1,6350 |
| 23 | CH$_2$F—CH$_2$O—(4-phenyl)- | 93–95 |

-continued

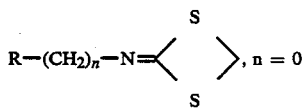, n = 0

| Example No | R | m.p. (C.) or $n_{20}^D$ |
|---|---|---|
| 24 | 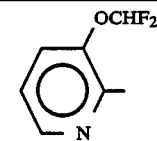 | 30–35 |
| 25 | 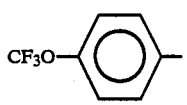 | 1,5827 |
| 26 | 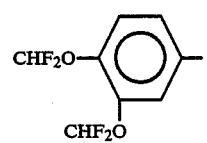 | 55–58 |
| 27 | 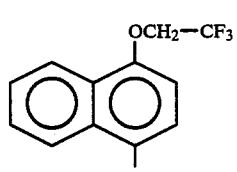 | 74–76 |
| 28 | 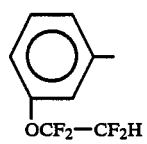 | 1,5648 |
| 29 | 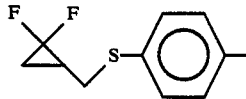 | 36–38 |
| 30 | 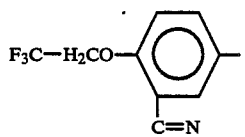 | 110 |
| 31 | 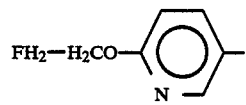 | 72–75 |
| 32 | 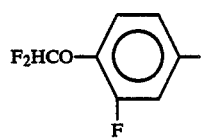 | 26–28 |
| 33 | 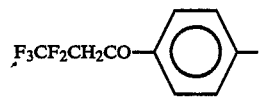 | 34 |

-continued

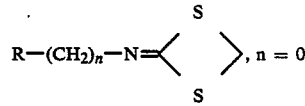, n = 0

| Example No | R | m.p. (C.) or $n_{20}^D$ |
|---|---|---|
| 34 | 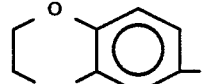 | 75 |
| 35 | 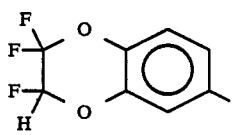 | 1,591 |
| 36 | 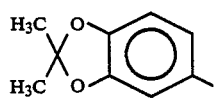 | 67 |
| 37 | 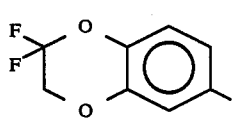 | 1,6504 |
| 38 |  | 53–55 |
| 39 | 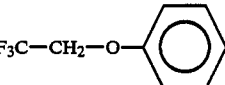 | 1,6140 |

| | R | n = 1 | |
|---|---|---|---|
| 40 | 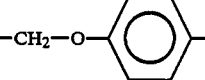 | | 1,5733 |

EXAMPLE 41

N-(2,2-Difluoro-1,3-benzodioxol-5-yl)-1,3-dithietan-2-imine 5.19 g (0.03 mol) 2,2-Difluoro-1,3-benzodioxol-5-amine was reacted with 2.51 g (0.033 mol) carbon disulphide were combined. Over 5 minutes at room temperature, 3.34 g (0.033 mol) triethylamine was added dropwise. The reaction mixture was then stirred at 70° C. (bath temperature) for 1 hour. After cooling it was treated with 50 ml diethyl ether, vigorously stirred and the crystals separated.

Yield: 7.54 g=70.9% of theory triethylammonium N-(2,2-difluoro-1,3-benzodioxol-5-yl)dithiocarbamate.

7.36 g (0.021 mol) Triethylammonium N-(2,2-difluoro-1,3-benzodioxol-5-yl)dithiocarbamate was dissolved in 50 ml dimethylformamide. With vigorous stirring, a mixture of 18.25 g (0.105 mol) dibromomethane and 2.12 g (0.021 mol) triethylamine in 20 ml dimethylformamide was added dropwise. It was then stirred for two hours. The reaction mixture was poured into 250 ml ice/water and extracted 3 times with 100 ml diethyl ether. The combined ether phases were dried over magnesium sulphate and concentrated. Purification was then carried out by column chromatography (eluent: hexane/ethyl acetate 4:1).

Yield: 4.20 g = 76.5% of theory
m.p.: 30°–32° C.

EXAMPLE 42

N-[2-(2,2,2-Trifluoroethoxy)-5-pyridyl]-1,3-dithietan-2l-imine, dihydrochloride 10.0 g (0.0357 mol) N-[2-(2,2,2-Trifluoroethoxy)-5-pyridyl]-1,3-dithietan-2-imine was dissolved in 300 ml diethyl ether and, under vigorous stirring and ice cooling, hydrogen chloride gas was passed therein. The precipitated crystals were separated and dried.

Yield: 12.3 g = 97.5% of theory
m.p.: 152°–154° C.

EXAMPLE 43

N-(2,2-Difluoro-1,3-benzodioxol-5-yl)-1,3-dithietan-2-imine, hydrochloride 10.0 g (0.0357 mol) N-(2,2-Difluoro-1,3-benzodioxol-5-yl)-1,3-dithietan-2-imine was dissolved in 300 ml diethyl ether and, under vigorous stirring and ice cooling, hydrogen chloride gas was passed in. The precipitated crystals were separated and dried.

Yield: 5.60 g = 94.1% of theory
m.p.: 170°–174° C.

In a similar manner the following acid addition salts were prepared:

$$R-(CH_2)_n-N=\!\!\!<\!\!\!\overset{S}{\underset{S}{\phantom{X}}}\!\!\!>\cdot HA \quad n = 0$$

| Example No | R | Acid HA | m.p. (°C.) or $n_{20}^D$ |
|---|---|---|---|
| 44 | CHF$_2$O—⟨phenyl⟩— | HCl | 180–181 |
| 45 | [CHF$_2$O—⟨phenyl⟩—]$_2$ | naphthalene-1,5-disulfonic acid (SO$_3$H, SO$_3$H) | 187–189 |
| 46 | CF$_3$CH$_2$S—⟨phenyl⟩— | HCl | 180–183 |
| 47 | CF$_3$—S—⟨phenyl⟩— | HCl | 181–183 |
| 48 | CHF$_2$—S—⟨phenyl⟩— | HCl | 162–164 |
| 49 | CHF$_2$—O—⟨phenyl⟩— | CF$_3$COOH | 60 |
| 50 | CHF$_2$—O—⟨phenyl⟩— | HI | 183 |
| 51 | CHF$_2$—O—⟨phenyl⟩— | H$_3$C—⟨phenyl⟩—SO$_3$H | 130 |

-continued $$R-(CH_2)_n-N=\underset{S}{\overset{S}{\left\langle \phantom{X} \right\rangle}} \cdot HA \quad n = 0$$

| Example No | R | Acid HA | m.p. (°C.) or $n_{20}^D$ |
|---|---|---|---|
| 52 | CHF₂O—⟨C₆H₄⟩— | H₂SO₄ | 164–167 |
| 53 | 3-OCHF₂-pyridin-2-yl | HCl | 165 |
| 54 | CF₃O—⟨C₆H₄⟩— | HCl | 171–174 |
| 55 | 3,4-(CHF₂O)₂—C₆H₃— | HCl | 181–185 |
| 56 | CHF₂—O—⟨C₆H₄⟩— | HBr | 190 |
| 57 | [CHF₂—S—⟨C₆H₄⟩—]₂ | naphthalene-1,5-disulfonic acid | 184 |
| 58 | BrF₂C—CO—⟨C₆H₄⟩— | HCl | 164 |
| 59 | [BrF₂C—CO—⟨C₆H₄⟩—]₂ | naphthalene-1,5-disulfonic acid | 179 |
| 60 | 3-F₃CH₂CO-4-CN—C₆H₃— | HCl | 186 |
| 61 | HF₂C—F₂CO—⟨C₆H₄⟩— | HCl | 155 |

-continued $$R-(CH_2)_n-N=\genfrac{}{}{0pt}{}{S}{S}\hspace{-1em}\bigg\rangle \cdot HA \quad n = 0$$

| Example No | R | Acid HA | m.p. (°C.) or $n_{20}^D$ |
|---|---|---|---|
| 62 | F$_2$HCO—⟨phenyl⟩— | CF$_3$SO$_3$H | 135 |
| 63 | F$_2$C(O—)(O—)⟨phenyl⟩— | H$_2$SO$_4$ | 157–159 |
| 64 | F$_2$C(O—)(O—)⟨phenyl⟩— ·½x | naphthalene-1,4-disulfonic acid (SO$_3$H / SO$_3$H) | 200 |
| 65 | F$_3$C-CHF-(O—)(O—)⟨phenyl⟩— | H$_2$SO$_4$ | 100 |
| 66 | (H$_3$C)(H$_3$C)C(O—)(O—)⟨phenyl⟩— | H$_2$SO$_4$ | 30 |
| 67 | (H$_3$C)(H$_3$C)C(O—)(O—)⟨phenyl⟩— | HCl | 109 |
| 68 | [(H$_3$C)(H$_3$C)C(O—)(O—)⟨phenyl⟩—]$_2$ | naphthalene-1,4-disulfonic acid (SO$_3$H / SO$_3$H) | 166 |

USE EXAMPLE 1

Control of root knot nematode (*Meloidogyne incognita*)

10% of powder preparations of active ingredients were mixed thoroughly with soil that had been strongly infested with the test nematode. After this the treated soil was put into a 0.5 liter fermenting tube, treated with cucumber seeds and cultivated at a soil temperature of 25° to 27° C. in a greenhouse. After a cultivation time of 25 to 28 days, the cucumber roots were washed and inspected in a water bath for nematode attack (root knots) and the % level of activity of the active ingredients compared with a treated control was determined. When the nematode attack is fully controlled the level of activity is 100%.

At a dose of 25 mg of active substance per liter of soil, a nematode attack by *Meloidogyne incognita* was fully controlled (100%) by compounds of Examples 1–3, 6, 7, 14, 19, 21, 23–25, 44, 45, 49–53 and 56.

USE EXAMPLE 2

Ovicidal and/or inhibition of hatching activity on egg masses of root knot nematode (*Miloidogyne incognita*) and cysts of the root cyst nematode (*Heterodera schachtii*)

Egg masses of *Miloidogyne incognita* and ready to hatch cysts of *Heterodera schachtii* were immersed for 48 hours in 0.0025% suspensions or emulsions of compounds of the invention, washed in running water and left at 25°–26° C. until larva emergence.

Compounds of examples 2, 3, 19, 21, 44, 45 and 49–52 fully inhibited (100% activity) the hatch of L$_2$ larvae of *Meloidogyne incognita* and of *Heterodera schachtii*.

USE EXAMPLE 3

Activity against larvae of the diamond-backed moth (*Plutella xylostella*)

The compounds of the invention were made up as aqueous suspensions or emulsions at a concentration of 0.1%. Cabbage leaves (*Brassica olearacea* var. *botrytis*), placed in polystyrene petri dishes, were sprayed with these preparations (4 mg spray/cm$^2$). After the sprayed surface had dried, 10 young larvae of the diamond-backed moth (*Plutella xylostella*) were placed in each petri dish and thereby exposed to the treated food in the closed dishes for two days. The % mortality of the larvae after two days indicated the level of activity.

Compounds of Examples 2, 3, 9, 17, 19 and 20 showed 100% activity.

USE EXAMPLE 4

Activity against larvae (L3) of the Mexican bean beetle (*Epilachna varivestis*)

The compounds of the invention were made up as aqueous suspensions or emulsions at a concentration of 0.1%. French bean plants (*Phaseolus vulgaris*) in the primary leaf stage were dipped in the preparations. For each test two plant stems with in total four primary leaves were placed in glass vases filled with water and enclosed in plexiglass cylinders. Then five larvae of the Mexican bean beetle (*Epilachna varivestis*) at the third larval stage were put in the glass cylinders and kept for three days under extended daylight conditions. The mortality of the larvae after three days indicated the level of activity.

Compounds of Examples 3, 17, 19 and 44 showed an 80 to 95% activity.

USE EXAMPLE 5

Ovicidal activity against eggs of the cotton army worm (*Spodoptera littoralis*)

The compounds of the invention were made up as aqueous suspensions or emulsions at a concentration of 0.1%. One day old eggs that had been laid on filter paper by fertilised female moths were dipped in the preparations until they were completely wet and then placed in closed petri dishes in the laboratory under extended daylight conditions for four days. The % inhibition of hatching of the eggs in comparison with untreated eggs indicates the level of activity.

Compounds of Examples 2, 9, 15, 21 and 33 showed an 80–100% activity.

USE EXAMPLE 6

Soil insecticide activity against eggs/larvae of the corn rootworm (*Diabrotica undecimpunctata*)

Formulations of compounds of the invention were made up with an active ingredient content of 0.04% by diluting emulsifiable concentrates with water to the desired concentration. 20 ml of this preparation was poured into each plastic flower pot (66×66×82 mm) each of which was filled with 200 l ml earth and ca. 100 eggs of the corn rootworm (*Diabrotica undecimpunctata*) as well as 2 grains of corn (*Zea mays*) at a depth of ca. 1 cm of soil. The pots were left in the glasshouse under extended daylight conditions and at 24°–26° C. for 14 days. The criterion for judging the activity was the emergence of maize plants in untreated pots with and without eggs within 14 days.

Compounds of Examples 21 and 33 showed undisturbed plant growth.

USE EXAMPLE 7

Activity in prophylactic treatment of leaves against brown rice-hoppers (*Niliparvata lugens* Stal)

In a heated greenhouse, rice seedlings (about 15 per pot) were grown until formation of the third leaf and then sprayed until dripping wet with an aqueous preparation containing 0.1% of active material. After drying the sprayed leaves, a transparent cylinder was placed over each pot. 30 Adult brown rice-hoppers (*Niliparvata lugens*) were introduced into each pot. After 2 days at 26° C. in the greenhouse, the amount of dead hoppers was determined. The activity was calculated according to Abbott in comparison with several untreated control pots.

90–100 mortality was reached with the compounds of Examples 8, 9, 10, 14, 15, 17, 19, 26, 31 and 44.

Even at a reduced concentration of 0.0064%, activities of 90% and greater were found with compounds 1, 2, 8, 12 and 13.

USE EXAMPLE 8

Activity in the curative treatment of broad beans (*Vicia fabae*) against black bean aphids (*Aphis fabae* scop.)

In a heated greenhouse, seedlings of broad beans (*Vicia fabae*) (one plant per pot) were grown to a height of about 6 cm. The plants were then covered with a culture of black bean aphid (*Aphis fabae*). After the each plant had been colonised with 100 to 200 insects, they were each sprayed with 0.1% aqueous preparations until dripping wet and left in the glasshouse at about 24° C. After 2 days the amount of dead aphids was ascertained. The activity was calculated according to Abbott by comparison with untreated controls indicated the level of activity.

With the compound of Example 2 an activity of more than 80% was achieved.

USE EXAMPLE 9

Activity in the curative treatment of field beans (*Phaseolus vulgaris* nanus Aschers.) against motile stages of the two spotted mite (*Tetranychus urticae* Koch)

In a heated greenhouse, seedlings of field beans were grown to full development of the primary leaf and then covered with bits of leaf infested with *Tetranychus urticae*. One day later the leaf bits were removed and the plants sprayed with 0.1% aqueous preparation of the active ingredient until dripping wet. After 7 days at 22° to 24° C., the amount of dead motile stages of Tetranychus on treated and untreated plants was ascertained. The activity was calculated according to Abbott.

For the compounds of Examples 2, 8, 10, 15, 17, 19, 26 and 33, 80–100% activity was found.

USE EXAMPLE 10

Activity in the curative treatment of field beans (*Phaseolus vulgaris* nanus Aschers.) against eggs of the two spotted mite (*Tetranychus urticae* Koch)

In a heated greenhouse, seedlings of field beans were grown to full development of the primary leaf and then treated with adult females of *Tetranychus urticae*. One day later the plants, carrying the eggs which had been laid in the meantime, were sprayed with 0.1% aqueous preparation of the active ingredient until dripping wet.

After 7 days at 22° to 24° C., the amount of dead motile stages of Tetranychus on treated and untreated plants was ascertained. The activity was calculated according to Abbott.

With compounds of Examples 2, 10, 14, 15, 17, 19, 21 26, 31, 33 and 44 an activity of 80–100% was achieved.

USE EXAMPLE 11

Insecticidal activity against *Lucilia sericata*

1 ml aliquots of an acetone solution containing test compound at various concentrations were applied to cotton wool dental rolls 1 cm×2 cm, contained in glass vials (2 cm diameter×5 cm long). After drying, the treated materials were then impregnated with 1 ml of nutrient solution, infested with first instar larvae of sheep blowfly (*Lucilia sericata*), closed by a cotton wool plug and held at 25° C. for 24 hours.

For the controls the mortality was <5% whereas the compounds of Examples 18, 21, 28, 35 and 58 had an LC$_{50}$ of 300 ppm or less.

USE EXAMPLE 12

Insecticidal activity against *Blattella germanica*

Aliquots of acetone solutions of test compounds at various concentrations were applied to glass plates (10 cm×10 cm). After evaporation of solvent, the treated surfaces, together with controls treated with acetone alone, were then infested with second instar nymphs of the German cockroach, (*Blattella germanica*), retained on the treated surface within PTFE-coated glass rings 6 cm in diameter and held for 24 hours at 22° C. The percentage mortality of the insects was then recorded.

Less than 5% mortality resulted in the control treatments whereas the compound of Examples 21 had an LD$_{50}$ of 100 mg/m$^2$ or less.

USE EXAMPLE 12

Tickicidal activity against *Boophilus microplus*

9 cm diameter filter papers were impregnated with 1 ml aliquots of acetone solutions of test compound at various concentrations. The papers were allowed to dry and then folded into envelopes in which cattle tick larvae, (*Boophilus microplus*) were enclosed and held at 25° C. and 80% R.H. for 48 hours. The percentage mortality of tick larvae was then recorded and compared with controls.

The controls gave a mortality of less than 5% whereas the compound of Examples 35 caused 50% mortality at a concentration of 300 ppm or less.

We claim:

1. 2-imino-1,3-dithietane of formula I

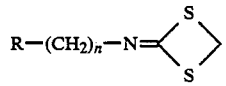

(I)

in which
R is the group

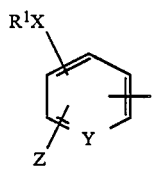

in which
Y is CH,
R$^1$ is fluoro-C$_{1-12}$-alkyl, fluoro-C$_{2-12}$-alkenyl, fluoro-C$_{2-12}$-alkynyl, fluorocyclopropyl or fluorocyclopropylmethyl;
X is oxygen or sulphur,
Z is hydrogen, halogen, C$_{1-6}$-alkyl, C$_{1-6}$-alkoxy, C$_{1-6}$-alkylthio, di-C$_{1-6}$-alkylamino, halo-C$_{1-6}$-alkyl, halo-C$_{1-6}$-alkoxy, halo-C$_{1-6}$-alkylthio, C$_{1-6}$-alkoxycarbonyl, halo-C$_{1-6}$-alkoxycarbonyl, nitro, cyano, amino, phenoxy, halophenoxy, phenylthio or halophenylthio, and
n is 0, 1 or 2, or an their acid addition salt thereof.

2. 2-imino-1,3-dithietane of claim 1 in which n is R$^1$ is CF$_3$, CHF$_2$, CF$_2$CHF$_2$ or CH$_2$CF$_2$CF$_3$ and Z is hydrogen or chloro.

3. 2-imino-1,3-dithietane according to claim 2 in which Z is hydrogen.

4. 2-imino-1,3-dithietane according to claim 3 in which X is oxygen.

5. 2-imino-1,3-dithietane according to claim 3 in which X is sulphur.

6. 2-imino-1,3-dithietane according to claim 5 in which R$^1$ is CF$_3$.

7. A pesticidal composition which comprises a compound claimed in claim 1, in admixture with an agriculturally acceptable diluent or carrier.

8. A pesticidal composition which comprises a compound claimed in claim 2, in admixture with an agriculturally acceptable diluent or carrier.

9. A pesticidal composition which comprises a compound claimed in claim 3, in admixture with an agriculturally acceptable diluent or carrier.

10. A pesticidal composition which comprises a compound claimed in claim 4, in admixture with an agriculturally acceptable diluent or carrier.

11. A pesticidal composition which comprises a compound claimed in claim 5, in admixture with an agriculturally acceptable diluent or carrier.

12. A pesticidal composition which comprises a compound claimed in claim 6, in admixture with an agriculturally acceptable diluent or carrier.

13. A method of combating pests, especially nematodes, which comprises applying to the insects or acarids or their locus an effective amount of a compound claimed in claim 1.

14. A method of combatting pests, especially nematodes, which comprises applying to the insects or acarids or their locus an effective amount of a compound claimed in claim 2.

15. A method of combatting pests, especially nematodes, which comprises applying to the insects or acarids or their locus an effective amount of a compound claimed in claim 3.

16. A method of combatting pests, especially nematodes, which comprises applying to the insects or acarids or their locus an effective amount of a compound claimed in claim 4.

17. A method of combatting pests, especially nematodes, which comprises applying to the insects or acarids or their locus an effective amount of a compound claimed in claim 5.

18. A method of combatting pests, especially nematodes, which comprises applying to the insects or acarids or their locus an effective amount of a compound claimed in claim 6.

* * * * *